(12) United States Patent
Sakai (10) Patent No.: US 8,581,210 B2
(45) Date of Patent: Nov. 12, 2013

(54) FLUORESCENCE INTENSITY COMPENSATION METHOD AND FLUORESCENCE INTENSITY COMPUTING APPARATUS

(75) Inventor: Yoshitsugu Sakai, Kanagawa (JP)

(73) Assignee: Sony Corporation, Tokyo (JP)

( * ) Notice: Subject to any disclaimer, the term of this patent is extended or adjusted under 35 U.S.C. 154(b) by 194 days.

(21) Appl. No.: 13/212,324

(22) Filed: Aug. 18, 2011

(65) Prior Publication Data

US 2012/0056103 A1 Mar. 8, 2012

(30) Foreign Application Priority Data

Sep. 3, 2010 (JP) ................................ 2010-197495

(51) Int. Cl.
*G01J 1/58* (2006.01)

(52) U.S. Cl.
USPC .................................... 250/459.1; 250/458.1

(58) Field of Classification Search
USPC .......................................... 250/458.1, 459.1
See application file for complete search history.

(56) References Cited

U.S. PATENT DOCUMENTS

2008/0212866 A1 9/2008 Lett et al.

FOREIGN PATENT DOCUMENTS

| EP | 1757223 | 2/2007 |
|---|---|---|
| JP | 2003-83894 | 3/2003 |
| WO | 9722848 | 6/1997 |

OTHER PUBLICATIONS

European Patent Office, Extended European Search Report, issued in connection with European Patent Application No. 11175562.5, dated Nov. 28, 2011. (8 pages).

Zimmerman, et al., "Spectral imaging and its applications in live cell microscopy," FEBS Letters, vol. 546, Issue 1, Jul. 3, 2003, pp. 87-92. (6 pages).

Tsurui et al., "Seven-color Fluorescence Imaging of Tissue Samples Based on Fourier Spectroscopy and Singular Value Decomposition," The Journal of Histochemistry & Cytochemistry, vol. 48, Issue 5, May 1, 2000, pp. 653-662. (8 pages).

Mark Berman, "Some Unmixing Problems and Algorithms in Spectroscopy and Hyperspectral Imaging," Proceedings of the 35th IEEE Applied Imagery and Pattern Recognition Workshop, Oct. 11-13, 2006. (8 pages).

*Primary Examiner* — Mark R Gaworecki
(74) *Attorney, Agent, or Firm* — K&L Gates LLP (57) ABSTRACT

A fluorescence intensity compensation method includes emitting light onto microparticles multiply labeled with a plurality of fluorochromes having fluorescence wavelength ranges that overlap each other in order to excite the fluorochromes and receiving fluorescence generated by the excited fluorochromes using photodetectors having different reception wavelength ranges, and computing fluorescence intensities of the fluorochromes by compensating detection values of the photodetectors under a predetermined constraint condition imposed on the computed fluorescence intensities.

4 Claims, 4 Drawing Sheets

BASIS FUNCTION $$\text{OBSERVATION POINT} \begin{array}{c} X_1 \\ X_2 \\ \vdots \\ \vdots \\ \vdots \\ X_N \end{array} \begin{pmatrix} \dfrac{X_1(x_1)}{\sigma_1} & \dfrac{X_2(x_1)}{\sigma_1} & \cdots & \dfrac{X_M(x_1)}{\sigma_1} \\ \dfrac{X_1(x_2)}{\sigma_2} & \dfrac{X_2(x_2)}{\sigma_2} & \cdots & \dfrac{X_M(x_2)}{\sigma_2} \\ \vdots & \vdots & & \vdots \\ \vdots & \vdots & & \vdots \\ \vdots & \vdots & & \vdots \\ \dfrac{X_1(x_N)}{\sigma_N} & \dfrac{X_2(x_N)}{\sigma_N} & \cdots & \dfrac{X_M(x_N)}{\sigma_N} \end{pmatrix}$$

with column headers $X_1()\quad X_2()\quad \cdots \quad X_M()$

FIG. 4

$$\begin{Bmatrix} FL1 \\ FL2 \\ FL3 \\ FL4 \\ FL5 \end{Bmatrix} = \begin{bmatrix} a_{11} & a_{21} & a_{31} & a_{41} & a_{51} \\ a_{12} & a_{22} & a_{32} & a_{42} & a_{52} \\ a_{13} & a_{23} & a_{33} & a_{43} & a_{53} \\ a_{14} & a_{24} & a_{34} & a_{44} & a_{54} \\ a_{15} & a_{25} & a_{35} & a_{45} & a_{55} \end{bmatrix}^{-1} \begin{Bmatrix} PMT1 \\ PMT2 \\ PMT3 \\ PMT4 \\ PMT5 \end{Bmatrix}$$

FL1 TO FL5: TRUE FLUORESCENCE INTENSITIES OF FLUOROCHROMES $a_{n1}$ TO $a_{n5}$: WAVELENGTH DISTRIBUTION COEFFICIENTS OF FLUOROCHROME n

PMT1 TO PMT5: MEASURED FLUORESCENCE INTENSITIES

FLUORESCENCE INTENSITY COMPENSATION METHOD AND FLUORESCENCE INTENSITY COMPUTING APPARATUS

CROSS REFERENCES TO RELATED APPLICATIONS

The present application claims priority to Japanese Priority Patent Application JP 2010-197495 filed in the Japan Patent Office on Sep. 3, 2010, the entire contents of which are hereby incorporated by reference.

BACKGROUND

The present application relates to a fluorescence intensity compensation method and a fluorescence intensity computing apparatus and, in particular, to a fluorescence intensity control method for accurately computing the intensity of fluorescence emitted from each of a plurality of fluorochromes multiply-labeled on a microparticle.

In order to measure a characteristic of a microparticle, such as a cell, existing apparatuses (e.g., flow cytometers) labels the microparticle using a fluorochrome, emits a laser beam onto the fluorochrome to excite the fluorochrome, and measures the intensity or pattern of the fluorescence emitted from the excited fluorochrome. In recent years, in order to more precisely analyze the characteristic of, for example, a cell, multi-color measurement has been used in which a microparticle is labeled using a plurality of fluorochromes and light beams emitted from the fluorochromes are measured using a plurality of photodetectors (e.g., PDs (photodiodes) or PMTs (photomultipliers)) having different wavelength ranges of received light. In multi-color measurement, in order to detect the fluorescence, one of optical filters is selected for a photodetector in accordance with the fluorescence wavelength of the fluorochrome being in use.

However, the currently used fluorochromes (e.g., FITC (fluorescein isothiocyanate) or PE (phycoerythrin)) have the overlap frequency range in the fluorescence spectrum. Accordingly, in the case where multi-color measurement is conducted using a combination of these fluorochromes, even when the fluorescence emitted from each of the fluorochromes is separated into individual frequency ranges using optical filters, the photodetectors may detect the fluorescence spilled over from an unwanted fluorochrome. If spillover of fluorescence occurs, the fluorescence intensity detected by the photodetector is shifted from the true intensity of fluorescence emitted from a desired fluorochrome. Thus, an error in a measurement arises.

In order to compensate the error in a measurement, fluorescence compensation is performed by subtracting the intensity of spillover fluorescence from the fluorescence intensity measured by the photodetector. The fluorescence compensation is performed by electrically or mathematically compensating a pulse so that the fluorescence intensity measured by the photodetector becomes a true fluorescence intensity of a desired fluorochrome.

Figure 3:
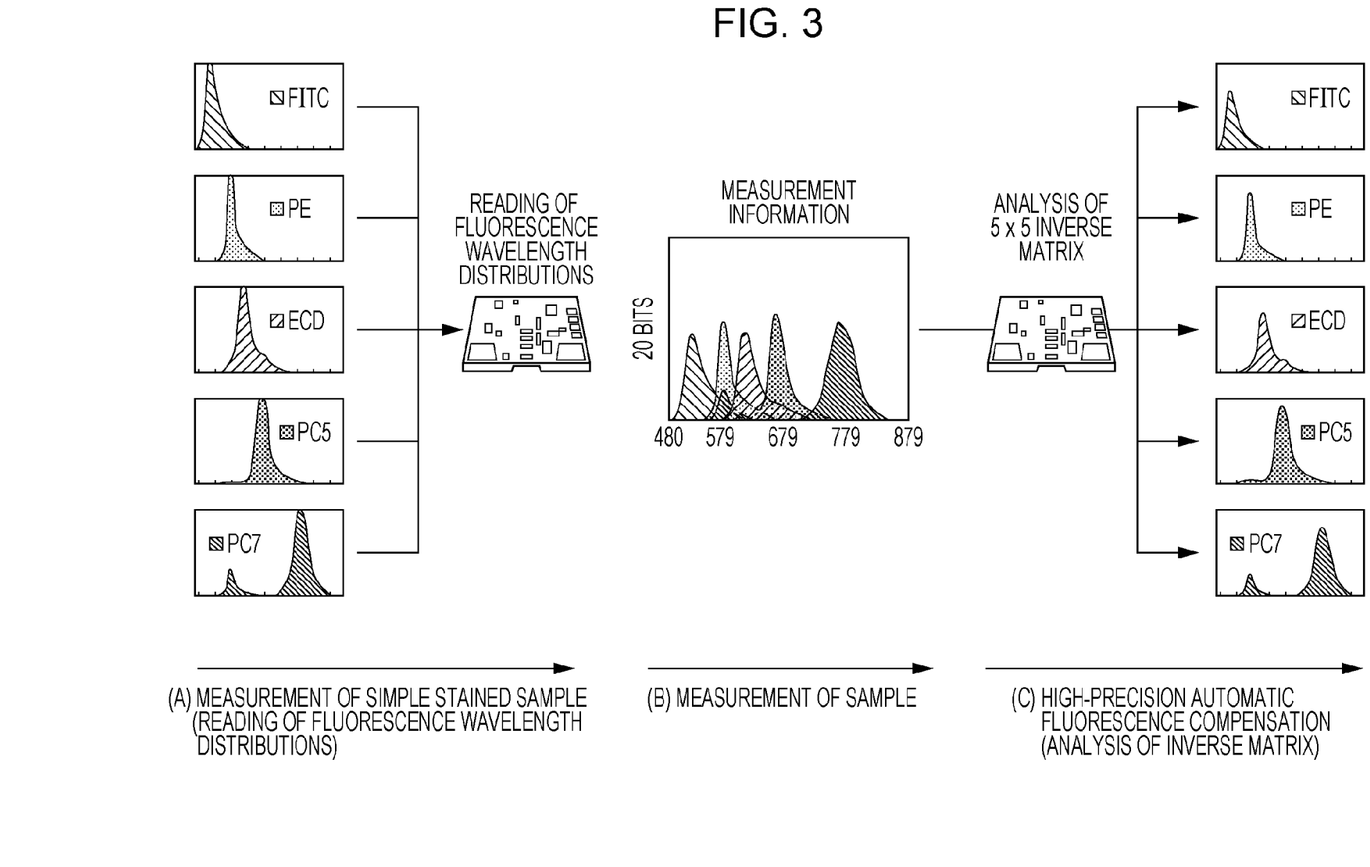
FIG. 3 illustrates a fluorescence compensation method using an existing compensation matrix.
Figure 4:
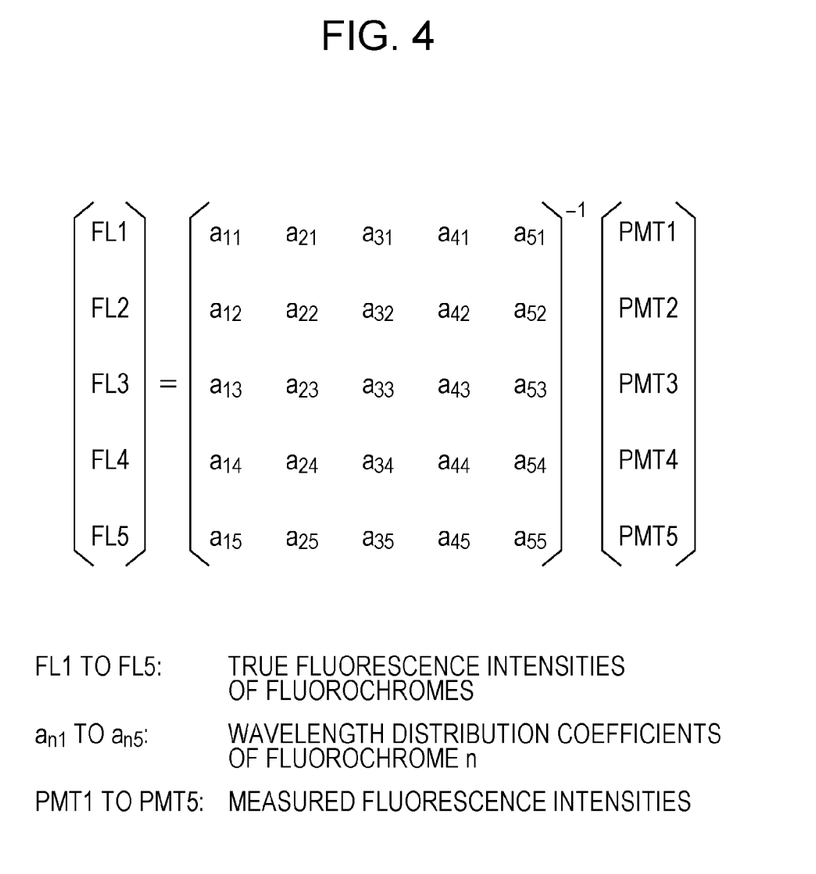
FIG. 4 illustrates elements of the existing compensation matrix.

A method for mathematically compensating the fluorescence intensity is performed by defining the fluorescence intensities (the detection values) measured by the photodetectors as a vector and applying the inverse matrix of a predetermined spillover matrix to the vector. In this way, a true intensity of the fluorescence emitted from a desired fluorochrome can be computed (refer to FIGS. 3 and 4 and Japanese Unexamined Patent Application Publication No. 2003-83894). The spillover matrix is generated by analyzing the fluorescence wavelength distribution of microparticles each of which is simple-labeled. In the spillover matrix, the fluorescence wavelength distribution of each of the fluorochromes is expressed as a column vector, and the column vectors are arranged. The inverse matrix of the spillover matrix is also referred to as a "compensation matrix". In FIGS. 3 and 4, the case in which five-color measurement is conducted using five types of fluorochrome (FITC, PE, ECD, PC5, and PC7) and five photodetectors is shown.

SUMMARY

In a method for compensating the fluorescence intensity using a compensation matrix, a negative value is allowed to be used as an element of the matrix. Accordingly, the compensated fluorescence intensity may be negative. This is because noise included in the detection value of each of the photodetectors has an effect on the value of an element of the matrix. However, in reality, the intensity of fluorescence emitted from each of the fluorochrome is not negative. In addition, if the intensity of fluorescence emitted from one of the fluorochromes is computed as a negative value, the computed values of the intensities of fluorescence emitted from other fluorochromes have an error in a positive direction.

If a subpopulation in which the fluorescence intensity of one of the fluorochromes is negative is present in a microparticle population to be analyzed, the subpopulation is not plotted in a two-dimensional correlation diagram (a cytogram) in which the fluorescence intensity of the fluorochrome is plotted on a logarithmic axis (with a logarithmic scale). Therefore, a user may misunderstand that the population plotted in the two-dimensional correlation diagram is less than the actual population.

In addition, in existing methods for compensating the fluorescence intensity, when the detection value of the intensity of autofluorescence emitted from a microparticle is regarded as the background and the intensity of autofluorescence is subtracted from the detection value of each of the photodetectors, an average value of the intensities of autofluorescence of the entirety of the population is used for computation. However, the intensity and the pattern of autofluorescence vary from subpopulation to subpopulation. Accordingly, the computation in which the same average value is subtracted from each of all of the populations causes an error in the computation value of the fluorescence intensity. In particular, if a variation in autofluorescence among subpopulations to be analyzed is significant, the error increases.

Accordingly, the present application provides a technique for accurately computing the intensity of fluorescence emitted from each of fluorochromes and presenting the computed intensity to a user when multi-color measurement of a microparticle that are multiply labeled with a plurality of fluorochromes is conducted using a plurality of photodetectors.

According to an embodiment, a fluorescence intensity compensation method includes emitting light onto microparticles multiply labeled with a plurality of fluorochromes having fluorescence wavelength ranges that overlap each other, exciting the fluorochromes, and receiving fluorescence generated by the excited fluorochromes using photodetectors having different reception wavelength ranges, and computing fluorescence intensities of the fluorochromes by compensating detection values of the photodetectors under a predetermined constraint condition imposed on the computed fluorescence intensities.

In computing fluorescence intensities, the fluorescence intensity of each of the fluorochromes and the autofluorescence intensity can be computed by approximating a measured spectrum obtained by collecting detection values of the photodetectors with a linear sum of a simple stainning spectrum obtained from the microparticle labeled with one of the fluorochromes and an autofluorescence spectrum obtained from the microparticle that is not labeled with any one of the fluorochromes. By performing computation while taking into account the autofluorescence component of the microparticle, the autofluorescence component that varies from subpopulation to subpopulation can be accurately computed and, therefore, the occurrence of a measurement error caused by a variation in the autofluorescence intensity from subpopulation to subpopulation can be prevented.

The constraint condition can be that each of the computed fluorescence intensity of each of the fluorochromes and the autofluorescence intensity is higher than or equal to a predetermined minimum value (for example, zero). By performing the computation under such a constraint condition, the occurrence of a measurement error and a decrease in the population in a two-dimensional correlation diagram (a cytogram) caused by a negative computed value of the fluorescence intensity of the fluorochrome can be prevented. The constraint condition can further include a condition that each of the computed fluorescence intensity and the autofluorescence intensity of each of the fluorochromes is lower than or equal to a predetermined maximum value.

The approximation using the linear sum of the simple stainning spectrum and the autofluorescence spectrum can be performed using a least-squares method. More specifically, the fluorescence intensity of each of the fluorochromes and the autofluorescence intensity are computed by obtaining parameters $a_k$ (k=1 to M) that minimize the following evaluation function:

$$\chi^2 \equiv \sum_{i=1}^{N} \left[ \frac{y_i - \sum_{k=1}^{M} a_k X_k(x_i)}{\sigma_i} \right]^2$$

where $X_k(x_i)$ denotes the simple staining spectrum of a k-th fluorochrome or the detection value of an i-th photodetector in the autofluorescence spectrum, $y_i$ denotes the detection value of the i-th photodetector in a measured spectrum, and $\sigma_i$ denotes the inverse number of a weight for the detection value of the i-th photodetector.

In addition, the present application provides a fluorescence intensity computing apparatus. The fluorescence intensity computing apparatus includes a measurement unit configured to emit light onto microparticles multiply labeled with a plurality of fluorochromes having fluorescence wavelength ranges that overlap each other, excite the fluorochromes, and receive fluorescence generated by the excited fluorochromes using photodetectors having different reception wavelength ranges and a computing unit configured to compute fluorescence intensities of the fluorochromes by compensating detection values of the photodetectors under a predetermined constraint condition imposed on the computed fluorescence intensities.

According to the present application, examples of the "microparticle" include a biologically-relevant microparticle, such as a cell, a microbe, and a liposome, and a synthetic particle, such as a latex particle, a gel particle, and an industrial particle. Examples of the biologically-relevant microparticle further include a chromosome, a liposome, a mitochondrion, and an organelle (a cell organelle). Examples of the cell include an animal cell (e.g., a blood cell) and a plant cell. Examples of the microbe include bacteria, such as bacteria coliform, a virus, such as a tobacco mosaic virus, and fungi, such as a rising. In addition, examples of the biologically-relevant microparticle include a nucleic acid, protein, and a biologically-relevant high molecular of a complex thereof. Furthermore, example of the industrial particle include an organic or inorganic high-polymer material and a metal. Examples of the organic high-polymer material include polystyrene, styrene-divinylbenzene, and polymethylmethacrylate. Examples of the inorganic high-polymer material include glass, silica, and a magnetic material. Examples of the metal include gold colloid and aluminum. In general, the microparticle is spherical. However, the microparticle may be nonspherical. In addition, the microparticle may have any size and any mass.

According to the present application, when a multi-color measurement of a microparticle labeled with a plurality of fluorochromes is performed using a plurality of photodetectors, a technology for accurately computing the fluorescence intensity of each of the fluorochromes and presenting the computed intensity to a user is provided.

Additional features and advantages are described herein, and will be apparent from the following Detailed Description and the figures.

DETAILED DESCRIPTION

Embodiments of the present application will be described below in detail with reference to the drawings.

Note that the following embodiments are merely for illustrative purposes only and are not meant to be limiting on the scope of the appended claims. Descriptions are made in the following order:

1. Method for Compensating Fluorescence Intensity
 (1) Measurement Step
 (2) Computation Step
 (2-1) Fitting Operation
 (2-1-1) Approximate Curve
 (2-1-2) Autofluorescence
 (2-1-3) Constraint Condition
 (2-2) Method for Computing $a_k$
 (2-2-1) Linear Least-Squares Method
 (2-2-2) Normal Equation
 (2-2-3) Singular Value Decomposition
2. Fluorescence Intensity Computing Apparatus
1. Method for Compensating Fluorescence Intensity According to the present application, a method for compensating a fluorescence intensity involves the following two steps: a measurement step and a computation step.

In the measurement step, a light beam is emitted onto a microparticle that is multiply labeled using a plurality of fluorochromes having an overlap fluorescence wavelength range, and the fluorescence emitted from the excited fluorochrome is received by a plurality of photodetectors having different reception wavelength ranges and, in the computation step, the intensity of fluorescence emitted from each of the fluorochromes is computed by compensating the detection value of each of the photodetectors under predetermined constraint conditions imposed on the computed fluorescence intensity.

(1) Measurement Step

A microparticle to be measured is multiply labeled using a plurality of fluorochromes. Fluorochrome labeling of a microparticle can be performed using an existing widely used method. For example, when a cell is measured, a fluorescence-labeled antibody for a cell-surface molecule is mixed with a cell. Thus, the antibody is coupled with the cell-surface molecule. The fluorescence-labeled antibody may be generated by directly coupling a fluorochrome to an antibody or by coupling a fluorochrome coupled with avidin to a biotin-labeled antibody using an avidin/biotin reaction. In addition, the antibody may be a monoclonal antibody or a polyclonal antibody.

As the fluorochromes, at least two materials can be selected from, for example, the following widely used materials: phycoerythrin (PE), FITC, PE-Cy5, PE-Cy7, PE-Texas red, allophycocyanin (APC), APC-Cy7, ethidium bromide, Propidium iodide, Hoechst 33258/33342, DAPI, acridine orange, chromomycin, mithramycin, olivomycin, pyronin y, thiazole orange, rhodamine 101, isothiocyanate, BCECF, BCECF-AM, C. SNARF-1, C. SNARF-1-AMA, aequorin, Indo-1, Indo-1-am, Fluo-3, Fluo-3-AM, Fura-2, Fura-2-AM, oxonol, texas red, rhodamine 123, 10-N-nony-acridine orange, fluorecein, fluorescein diacetate, carboxyfluorescein, caboxyfluorescein diacetate, carboxydichlorofluorescein, and carboxydichlorofluorescein diacetate.

Subsequently, a light beam is emitted onto the microparticle multiply labeled with the plurality of fluorochromes, and fluorescence emitted from the excited fluorochromes is received by a plurality of photodetectors having different reception wavelength ranges. The measurement step can be performed as in the method using a widely used multi-color measurement flow cytometer.

(2) Computation Step

In the computation step, the intensity of fluorescence emitted from each of the fluorochromes is computed by compensating the detection value of each of the photodetector acquired in the measurement step. At that time, in the method for compensating the fluorescence intensity according to the present embodiment, the fluorescence intensity is compensated under the constraint condition that the computed fluorescence intensity is higher than or equal to a predetermined minimum value.

The computation for compensation can be performed using an existing method in which a compensation matrix is employed. Alternatively, the computation for compensation can be performed using a fitting operation in which a measured spectrum obtained by collecting the detection values of the photodetectors is approximated with the linear sum of a simple stainning spectrum obtained from microparticles each labeled by one of the fluorochromes. An example of a fitting operation is described in detail below.

(2-1) Fitting Operation (2-1-1) Approximate Curve

In a fitting operation, a true fluorescence intensity emitted from each of the fluorochromes is computed by approximating the measured spectrum with the liner sum of a single stain spectrum. At that time, a true fluorescence intensity may be computed by approximating the measured spectrum with the liner sum of a simple stainning spectrum and the autofluorescence spectrum. As used herein, the term "measured spectrum" refers to a collection of the detection values of the photodetectors that have different reception wavelength ranges and that receive the fluorescence emitted from fluorochromes excited when light is emitted onto the microparticle multiply labeled with the fluorochromes having fluorescence wavelength ranges that overlap one another. In addition, the term "simple stainning spectrum" refers to a fluorescence wavelength distribution of each of the fluorochromes. The simple stainning spectrum can be obtained by collecting the detection value of a photodetector that receives the fluorescence emitted from a fluorochrome excited when light is emitted onto a microparticle labeled with the fluorochrome. Furthermore, the term "autofluorescence spectrum" refers to a wavelength distribution of the fluorescence originally emitted from the microparticle. By emitting light onto the microparticle that is not labeled with a fluorochrome, the fluorescence emitted from the microparticle is received by a photodetector. Thus, the detection value is collected to obtain the autofluorescence spectrum. The spectrum components of the above-described measured spectrum include the autofluorescence spectrum.

An approximate curve obtained by approximating the measured spectrum with the linear sum of a simple stainning spectrum is described next with reference to FIG. 1.

Figure 1:
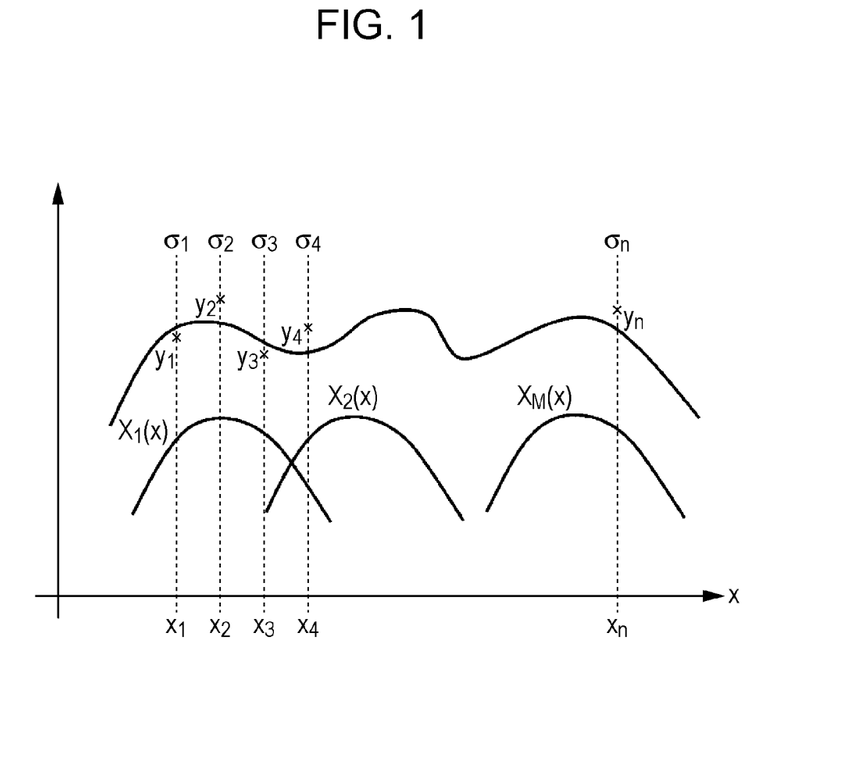
FIG. 1 is a graph illustrating an approximate curve obtained by approximating a measured spectrum with the linear sum of a simple stainning spectrum.

In FIG. 1, the X-axis represents an observation point, and the Y-axis represents the detection value. $y_1$ represents the detection value of the fluorescence received by a photodetector $x_1$. $y_2$ represents the detection value of the fluorescence received by a photodetector $x_2$. $y_n$ represents the detection value of the fluorescence received by a photodetector $x_n$. The curve connecting $y_1$ to $y_n$ represents a measured spectrum.

In addition, in FIG. 1, the curve (the basis function) representing a simple stainning spectrum of a first fluorochrome (a fluorochrome 1) is denoted as $X_1(x)$. The curve representing a simple stainning spectrum of a second fluorochrome (a fluorochrome 2) is denoted as $X_2(x)$. The curve representing a simple stainning spectrum of an Mth fluorochrome (a fluorochrome M) is denoted as $X_M(x)$. A simple stainning spectrum may be obtained by preparing a sample labeled with one of the fluorochromes every time a measurement is conducted. Alternatively, a prestored reference spectrum may be used.

Each of the photodetectors receives the fluorescence emitted from all of the fluorochromes (the fluorochromes 1 to M) in predetermined spillover coefficients. Accordingly, the detection value of each of the photodetectors can be approximated by the sum of values obtained by multiplying each of the basis functions of the fluorochromes 1 to M by a corresponding predetermined coefficient as follows:

$$y(x) = \sum_{k=1}^{M} a_k \cdot X_k(x) \tag{1}$$

Note that a fluorescence spillover coefficient $a_k$ from each of the fluorochromes into one of the photodetectors is determined by the emission intensity of the fluorochrome (a true fluorescence intensity).

More specifically, for example, the detection value $y_1$ of the photodetector $x_1$ can be approximated as a sum $y(x_1)$ obtained by summing a value obtained by multiplying the fluorescence intensity $X_1(x_1)$ of the fluorochrome 1 by the coefficient $a_1$ to a value obtained by multiplying the fluorescence intensity $X_M(x_1)$ of the fluorochrome M by the coefficient $a_M$. Note that the fluorescence spillover coefficients $a_k$ (k=1 to M) from the fluorochromes 1 to M into the photodetector $x_1$ correspond to the emission intensities of the fluorochromes 1 to M.

(2-1-2) Autofluorescence

The spectral components of the measured spectrum include the autofluorescence spectrum. Accordingly, the measured spectrum may be approximated with the liner sum of the simple stainning spectrum and the autofluorescence spectrum. The autofluorescence spectrum can be obtained by preparing a sample that is not labeled every time a measurement is conducted. Alternatively, a prestored reference spectrum may be used. When computation is performed by additionally using the detection values caused by the autofluorescence of the microparticle, the basis function $X_M(x_1)$ of the fluorochrome M is defined by, in equation (1), adding a curved line indicating the autofluorescence spectrum to the curved line indicating the simple stainning spectrum of the fluorochrome. The autofluorescence spectrum may vary from subpopulation to subpopulation of the microparticle. Accordingly, if the sample includes a plurality of subpopulations, a plurality of the basis functions $X_M(x)$ each set for one of the subpopulations are used.

Each of the photodetectors receives the fluorescence emitted from the fluorochrome and the autofluorescence component in a predetermined proportion. Therefore, the detection value of each of the photodetectors can be approximated with the sum of the basis functions of the fluorochromes multiplied by a predetermined coefficient and the basis function of the autofluorescence multiplied by a predetermined coefficient. At that time, the fluorescence spillover coefficient $a_k$ for each of the photodetectors is determined by the emission intensity of the autofluorescence (a true the fluorescence intensity).

More specifically, for example, a detection value $y_1$ of the photodetector $x_1$ can be approximated with a sum $y(x_1)$ of the sum of a value obtained by multiplying the fluorescence intensity $X_1(x_1)$ of the fluorochrome 1 by the coefficient $a_1$ to the fluorescence intensity $X_L(x_1)$ of the fluorochrome L by the coefficient $a_L$ and the sum of a value obtained by multiplying the fluorescence intensity $X_{L+1}(x_1)$ of the autofluorescence (L+1) by the coefficient $a_{L+1}$ to the fluorescence intensity $X_M(x_1)$ of the autofluorescence M by the coefficient $a_M$. The fluorescence spillover coefficient $a_k$ (k=(L+1) to M) for the photodetector $x_1$ corresponds to the emission intensity of the autofluorescence. Note that L is an integer ranging from 1 to M and is set in accordance with the number of fluorochromes being in use and the number of subpopulations of the microparticle in the sample.

In existing methods for compensating the fluorescence intensity, the average value of the autofluorescence intensities in the entirety of the population is regarded as the background, and the average value is subtracted from the detection value of each of the photodetectors. Accordingly, variations in the intensity and the pattern of the autofluorescence from subpopulation to subpopulation are not taken into account when computation is performed. This is a major reason for causing an error in a computed value of the fluorescence intensity. In the method for compensating the fluorescence intensity according to the present application, computation is performed while taking into account the autofluorescence component of a microparticle. Thus, the autofluorescence component that varies from subpopulation to subpopulation can be accurately computed and, therefore, a measurement error caused by the variation in the autofluorescence intensity from subpopulation to subpopulation can be removed.

Like the intensity of fluorescence emitted from a fluorochrome, the information regarding the computed autofluorescence intensity of each of the subpopulations may be displayed in a two-dimensional correlation diagram (a cytogram) and may be presented to a user. Thus, the user can select a desired subpopulation (perform gating) or identify the type of microparticle and the state of the microparticle in accordance with the level of the autofluorescence intensity. In this way, a novel analyzing method can be provided.

(2-1-3) Constraint Condition

The approximate curve represented by equation (1) can be obtained by computing $a_k$ using a linear least-squares method described below. $a_k$ is equivalent to the true fluorescence intensity of each of the fluorochromes or the autofluorescence intensity of the microparticle. Thus, physically, $a_k$ is not a negative value. Accordingly, in the method for compensating the fluorescence intensity according to the present application, compensation computation is performed for $a_k$ under the predetermined condition that $a_k$ is higher than or equal to a predetermined minimum value (a lower limit condition). For example, the minimum value used for the constraint condition can be zero, since the fluorescence intensity of each of the fluorochromes or the autofluorescence intensity of the microparticle is not negative. Alternatively, a value greater than zero can be used as the minimum value. Furthermore, compensation computation may be performed under an additional second constraint condition that $a_k$ is lower than a predetermined maximum value (a higher limit condition).

By performing compensation computation under the lower limit condition, a problem of a measurement error occurring when the fluorescence intensity of the fluorochrome is computed as a negative value and a problem of a decrease in a population in a two-dimensional correlation diagram (a cytogram) can be solved.

In addition, the intensity of autofluorescence is lower than the fluorescence intensity of a fluorochrome. Therefore, the quality of a signal of the autofluorescence is low. Thus, the computed autofluorescence intensity value is significantly affected by noise included in the detection value of each of the photodetectors and, therefore, an error occurs. By performing computation under the lower limit condition and/or the upper limit condition, a problem of a measurement error caused by noise can be solved.

In particular, when the intensity of autofluorescence of a microparticle to be measured is high and the fluorescence intensity of the fluorochrome is relatively low, it is difficult to determine whether the fluorescence of the microparticle is negative or positive. By imposing the zero lower limit condition on the detected autofluorescence value, the detection value for negative data becomes zero at all times. Therefore, even when the fluorescence intensity of the fluorochrome is relatively low, determination of positive data can be easily made.

(2-2) Method for Computing $a_k$
(2-2-1) Linear Least-Squares Method

A procedure for obtaining $a_k$ is described in detail below. Description is made with reference to the case in which a measured spectrum is approximated with only the linear sum of the simple stainning spectrum. However, this procedure is applicable to the case in which a measured spectrum is approximated with the linear sum of the simple stainning spectrum and the autofluorescence spectrum. First, an evaluation function (chi-square) represented by the following equation (2) below is defined:

$$\chi^2 \equiv \sum_{i=1}^{N} \left[ \frac{y_i - \sum_{k=1}^{M} a_k X_k(x_i)}{\sigma_i} \right]^2 \qquad (2)$$

where σi denotes the inverse of a weight for a measurement value of an i-th photodetector (e.g., the measurement error variance for the i-th photodetector. If such the inverse of a weight is not present, "1" may be used for all the photodetector). Subsequently, parameters $a_k$ (k=1 to M) that minimize equation (2) are computed.

(2-2-2) Normal Equation

Figure 2:
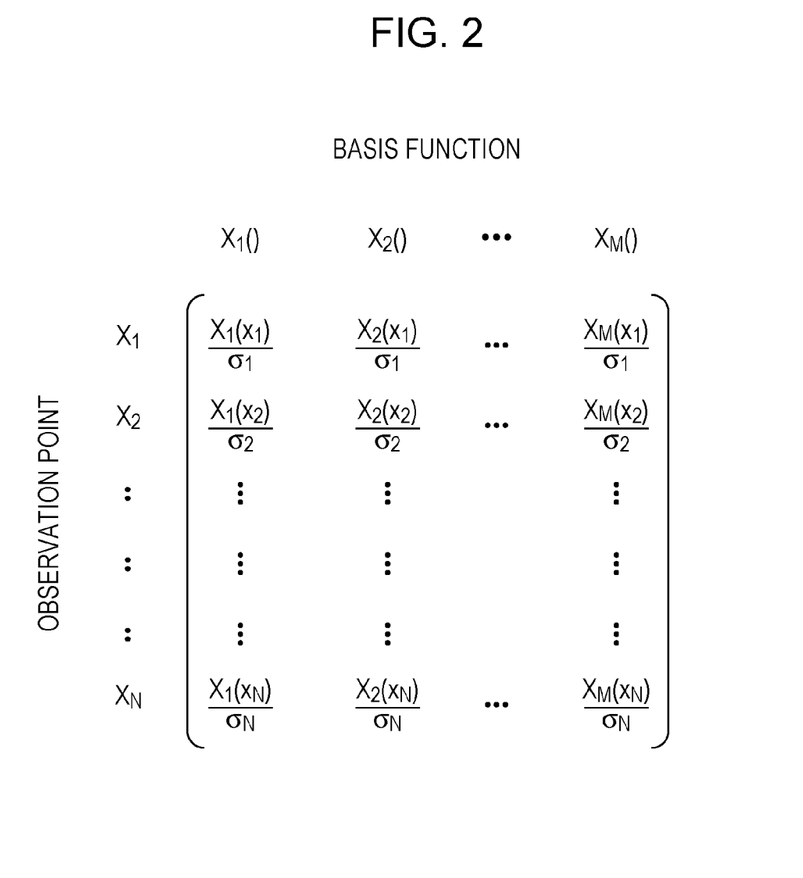
FIG. 2 illustrates elements of an N×M matrix A.

Thereafter, an N×M matrix A (refer to FIG. 2) including elements represented by equation (3) and a vector b having a length of N (refer to equation (4) below) are defined. Then, a vector a is defined by arranging M parameters $a_1$ to $a_M$ obtained by fitting.

$$A_{ij} = \frac{X_j(x_i)}{\sigma_i} \quad (3)$$

$$b_i = \frac{y_i}{\sigma_i} \quad (4)$$

The above-described equation (2) is minimized when all values obtained by differentiating $\chi^2$ with respect to the M parameters $a_k$ are zero.

$$0 = \sum_{i=1}^{N} \frac{1}{\sigma_i^2}\left[y_i - \sum_{j=1}^{M} a_j X_j(x_i)\right] \cdot X_k(x_i) \quad k=1,\ldots,M \quad (5)$$

By changing the summation order, equation (5) can be rewritten into the following form of a matrix equation (a normal equation):

$$\sum_{j=1}^{M} a_{kj} a_j = \beta_k \quad (6)$$

where $[a_{kj}]$ is an M×M matrix, and $[\beta_k]$ is a vector having a length of M.

$$a_{kj} = \sum_{i=1}^{N} \frac{X_j(x_i) \cdot X_k(x_i)}{\sigma_i^2} \quad \text{i.e., } [\alpha] = A^T \cdot A \quad (7)$$

$$\beta_k = \sum_{i=1}^{N} \frac{y_i \cdot X_k(x_i)}{\sigma_i^2} \quad \text{i.e., } [\beta] = A^T \cdot b \quad (8)$$

Accordingly, equation (5) can be rewritten into the following matrix form:

$$[\alpha] \cdot a = [\beta] \text{ or } (A^T \cdot A) \cdot a = A^T \cdot b \quad (9)$$

Equation (9) represents M simultaneous linear equations. By solving equation (9), $a_j$ can be obtained.

(2-2-3) Singular Value Decomposition

Instead of employing the method using the above-described normal equation, a vector a in which M parameters $a_1$ to $a_M$ are arranged may be computed using singular value decomposition.

Singular value decomposition (SVD) is based on a linear algebraic theorem describing that any N×M matrix A can be rewritten into the product of three matrices U, W, and $V^T$ (refer to equation (10) below). The matrix U is an N×M column-orthogonal matrix, the matrix W is an M×M diagonal matrix (diagonal elements $w_i$ are non-negative and are referred to as "singular values"), and the matrix $V^T$ is the transpose of an M×M orthogonal matrix V. In addition, the matrices U and V are orthonormal matrices in which all columns are orthonormal (refer to equation (11) below).

$$A = UWV^T \quad (10)$$

$$= U \cdot \begin{pmatrix} w_1 & & 0 \\ & w_2 & \\ & & \ddots \\ 0 & & w_M \end{pmatrix} \cdot V^T$$

$$U^T \cdot U = V^T \cdot V = 1 \quad (11)$$

The above-described equation (2) can be rewritten as follows:

$$\chi^2 = |A \cdot a - b|^2 \quad (12)$$

When the matrix A is subjected to singular value decomposition and the matrices U, W, and V are obtained as in equation (10), a vector a that minimizes equation (12) can be computed as follows:

$$a = V \cdot [\text{diag}(1/w_j)] \cdot (U^T \cdot b) \quad (13)$$

This operation is referred to as "backward substitution". If a sufficiently small value of wi is found, 1/wi is replaced with 0, and the processing proceeds.

2. Fluorescence Intensity Computing Apparatus

According to the embodiment, like an existing flow cytometer, a fluorescence intensity computing apparatus includes a fluid-structure system, an optical system, a sorting system, and a data processing system.

The fluid-structure system causes sample liquid including microparticles to be measured to flow in the center of laminar flow of sheath fluid so that the microparticles are arranged in a flow cell in line. Instead of a flow cell, the microparticles are arranged in line in a flow path formed on a microchip.

The optical system serves as a measurement unit that emits light onto the microparticle labeled with a fluorochrome, excites the fluorochrome, and receives fluorescence generated by the excited fluorochrome. The optical system also detects front scattered light, side scattered light, and scattered light such as Rayleigh scattering and Mie scattering. More specifically, the optical system includes a light emitting subsystem having a laser light source, a collecting lens, a diachronic mirror, and a bandpass filter used for collecting and emitting the laser beam from and to a microparticle and a detecting sub-system for detecting the fluorescence emitted from the microparticle due to emission of a laser beam and scattered light. For example, the detecting sub-system includes area image pickup elements, such as photo multiplier tubes (PMTs), CCDs, or CMOS elements. In the detecting sub-system, a plurality of the photodetectors having different reception wavelength ranges are arranged.

When sorting the microparticles, sample liquid is ejected to a space outside the flow cell in the form of a droplet including the microparticle and a direction in which the droplet moves is controlled. Thus, the microparticle having a desired characteristic is sorted. The sorting system includes a vibration element (e.g., a piezoelectric element) that changes the sample liquid into droplets and ejects the droplets, a charging unit that charges the ejected droplets, and a pair of electrodes that face each other with the moving droplet therebetween.

The data processing system receives the detection value of the photodetector in the form of an electrical signal and analyzes the optical characteristic of the microparticle on the basis of the electrical signal. The data processing system approximates the measured spectrum with the linear sum of the simple stainning spectrum and the autofluorescence spectrum using the above-described technique and computes the true fluorescence intensity of each of the fluorochromes and the autofluorescence intensity of the microparticle. In order to perform computation, the data processing system includes a recording medium (e.g., a hard disk) for storing a program that follows the steps of the above-described fluorescence intensity computing method and a central processing unit (CPU) and a memory used for executing the program.

In order to increase the quality of the signal output from each of the photodetectors, it is desirable that the data processing system include a noise filter that smoothes the data exchanged among the photodetectors. An averaging operation is performed while taking into account, for example, the number of the photodetectors, the reception wavelength range, the fluorochromes being in use, the autofluorescence wavelength, and the noise frequency component of each of the devices. By smoothing the data, the negative impact of noise can be reduced and, therefore, the computation accuracy can be increased. As a result, the fluorescence intensity can be more accurately computed.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A fluorescence intensity compensation method comprising:
    emitting light onto a microparticle multiply labeled with a plurality of fluorochromes having fluorescence wavelength ranges that overlap each other in order to excite the fluorochromes and receiving fluorescence generated by the excited fluorochromes using photodetectors having different reception wavelength ranges; and
    computing fluorescence intensities of the fluorochromes by compensating detection values of the photodetectors under a predetermined constraint condition imposed on the computed fluorescence intensities,
    wherein the constraint condition is that each of the computed fluorescence intensity of each of the fluorochromes and an autofluorescence intensity is higher than or equal to a predetermined minimum value,
    wherein the constraint condition further includes a condition that each of the computed fluorescence intensity of each of the fluorochromes and the autofluorescence intensity is lower than or equal to a predetermined maximum value, and
    wherein in computing fluorescence intensities, an approximation of a measured spectrum using a linear sum of a simple staining spectrum and an autofluorescence spectrum is performed using a least-squares method.

2. The fluorescence intensity compensation method according to claim 1, wherein in computing fluorescence intensities, the fluorescence intensity of each of the fluorochromes and the autofluorescence intensity are computed by approximating the measured spectrum obtained by collecting detection values of the photodetectors using the linear sum of the simple staining spectrum obtained from a microparticle labeled with one of the fluorochromes and the autofluorescence spectrum obtained from a microparticle that is not labeled with any one of the fluorochromes.

3. The fluorescence intensity compensation method according claim 1, wherein in computing fluorescence intensities, the fluorescence intensity of each of the fluorochromes and the autofluorescence intensity are computed by obtaining parameters $a_k$ (k=1 to M) that minimize the following evaluation function:

$$\chi^2 \equiv \sum_{i=1}^{N} \left[ \frac{y_i - \sum_{k=1}^{M} a_k X_k(x_i)}{\sigma_i} \right]^2$$

where $X_k(x_i)$ denotes the simple staining spectrum of a k-th fluorochrome or the detection value of an i-th photodetector in the autofluorescence spectrum, $y_i$ denotes the detection value of the i-th photodetector in a measured spectrum, and $\sigma_i$ denotes the inverse number of a weight for the detection value of the i-th photodetector.

4. A fluorescence intensity computing apparatus comprising:
    a measurement unit configured to emit light onto a microparticle multiply labeled with a plurality of fluorochromes having fluorescence wavelength ranges that overlap each other in order to excite the fluorochromes and receive fluorescence generated by the excited fluorochromes using photodetectors having different reception wavelength ranges; and
    a computing unit configured to compute fluorescence intensities of the fluorochromes by compensating detection values of the photodetectors under a predetermined constraint condition imposed on the computed fluorescence intensities,
    wherein the constraint condition is that each of the computed fluorescence intensity of each of the fluorochromes and an autofluorescence intensity is higher than or equal to a predetermined minimum value,
    wherein the constraint condition further includes a condition that each of the computed fluorescence intensity of each of the fluorochromes and the autofluorescence intensity is lower than or equal to a predetermined maximum value, and wherein the computing unit is configured to perform an approximation of a measured spectrum using a linear sum of a simple staining spectrum and a autofluorescence spectrum using a least-squares method.

* * * * *